United States Patent
Kayo et al.

(10) Patent No.: US 10,597,406 B2
(45) Date of Patent: *Mar. 24, 2020

(54) PURIFICATION OF RAPAMYCIN DERIVATIVES USING TEMPERATURE INDUCED PHASE SEPARATION

(71) Applicant: Biosensors International Group, Ltd., Hamilton (BM)

(72) Inventors: Margaret W. Kayo, Los Altos, CA (US); Richard S. Fornicola, Devens, MA (US); Ivan Kovacik, Devens, MA (US); Leelakrishna Kondaveti, Devens, MA (US); Aniruddh Singh, Devens, MA (US)

(73) Assignee: Biosensors International Group, Ltd., Hamilton (BM)

( * ) Notice: Subject to any disclaimer, the term of this patent is extended or adjusted under 35 U.S.C. 154(b) by 0 days.

This patent is subject to a terminal disclaimer.

(21) Appl. No.: 16/224,140

(22) Filed: Dec. 18, 2018

(65) Prior Publication Data

US 2019/0256527 A1 Aug. 22, 2019

Related U.S. Application Data

(63) Continuation of application No. 15/422,593, filed on Feb. 2, 2017, now Pat. No. 10,202,402, which is a continuation of application No. 14/853,711, filed on Sep. 14, 2015, now Pat. No. 9,598,439, which is a continuation of application No. PCT/US2014/030602, filed on Mar. 17, 2014.

(60) Provisional application No. 61/799,857, filed on Mar. 15, 2013.

(51) Int. Cl.
*C07D 498/18* (2006.01)
(52) U.S. Cl.
CPC .................. *C07D 498/18* (2013.01)
(58) Field of Classification Search
CPC .................................................. C07D 498/18
See application file for complete search history.

(56) References Cited

U.S. PATENT DOCUMENTS

| | | |
|---|---|---|
| 6,423,722 B1 | 7/2002 | Dosenbach et al. |
| 7,220,755 B2 | 5/2007 | Betts et al. |
| 7,232,486 B2 | 6/2007 | Keri et al. |
| 7,384,953 B2 | 6/2008 | Shaw et al. |
| 7,473,366 B2 | 1/2009 | Patil et al. |
| 7,700,614 B2 | 4/2010 | Dhaon et al. |
| 7,820,812 B2 | 10/2010 | Viswanath et al. |
| 8,138,344 B2 | 3/2012 | Acemoglu et al. |
| 9,598,439 B2 | 3/2017 | Kayo et al. |
| 10,202,402 B2 | 2/2019 | Kayo et al. |
| 2004/0266703 A1 | 12/2004 | Keri et al. |
| 2006/0198867 A1 | 9/2006 | Toner et al. |
| 2007/0128731 A1 | 6/2007 | Deshmukh et al. |
| 2008/0146796 A1 | 6/2008 | Kawanishi et al. |
| 2008/0287675 A1 | 11/2008 | Li |
| 2010/0029933 A1 | 2/2010 | Patil et al. |
| 2010/0272773 A1 | 10/2010 | Kangas et al. |
| 2011/0009325 A1 | 1/2011 | Viswanath et al. |
| 2013/0035483 A1 | 2/2013 | Zeng et al. |
| 2013/0053947 A1 | 2/2013 | Kangas et al. |
| 2016/0002262 A1 | 1/2016 | Kayo et al. |
| 2017/0334928 A1 | 11/2017 | Kayo et al. |

FOREIGN PATENT DOCUMENTS

| | | |
|---|---|---|
| JP | 2007532134 A | 11/2007 |
| WO | 2006060616 A1 | 6/2006 |
| WO | 2007103348 A2 | 9/2007 |
| WO | 2013028208 A1 | 2/2013 |

OTHER PUBLICATIONS

Chalmers et al., "Vibrational Spectroscopic Methods in Phamnaceutical Solid-State Charcterization", Chapter 5, Polymorphism in the Pharmaceutical Industry. R. Hilfiker, Wiley-VCH Verlag GmbH & Co. KGaA, Weinheim, May 22, 2016, pp. 95-138.
Craig , "Characterization of Polymorphic Systems Using Thermal Analysis", Chapter 3, Polymorphism in the Pharmaceutical Industry. R. Hilfiker, Wiley-VCH Verlag GmbH & Co. KGaA, Weinheim, May 22, 2016, pp. 43-79.
Yu, "Amorphous Pharmaceutical Solids: Preparation, Characterization and Stabilization", Advanced Drug Delivery Reviews, vol. 48, Issue 1, May 16, 2001, pp. 27-42.
EP14763326.7 , "Extended European Search Report", dated Nov. 21, 2016, 9 pages.
EP14763326.7 , "Partial Supplementary European Search Report", dated Aug. 18, 2016, 6 pages.
PCT/US2014/030602 , "International Search Report and Written Opinion", dated Aug. 19, 2014, 11 pages.

*Primary Examiner* — Bruck Kifle
(74) *Attorney, Agent, or Firm* — Kilpatrick Townsend & Stockton LLP

(57) ABSTRACT

The present invention provides methods for obtaining purified rapamycin derivatives, including purified Biolimus A9. A crystalline form of Biolimus A9 is also described.

18 Claims, 7 Drawing Sheets

PURIFICATION OF RAPAMYCIN DERIVATIVES USING TEMPERATURE INDUCED PHASE SEPARATION

CROSS-REFERENCES TO RELATED APPLICATIONS

The present application is a continuation of U.S. patent application Ser. No. 15/422,593, filed Feb. 2, 2017, which is a continuation of U.S. patent application Ser. No. 14/853,711, filed Sep. 14, 2015, (now U.S. Pat. No. 9,598,439, issued Mar. 21, 2017) which is a continuation of International Application No. PCT/US2014/030602, filed Mar. 17, 2014, which claims priority to U.S. Provisional Patent Application No. 61/799,857, filed Mar. 15, 2013, the disclosures of which are incorporated herein by reference in their entirety.

BACKGROUND OF THE INVENTION

This invention provides for an economic and effective means to purify 40-O-rapamycin derivatives from unwanted byproducts having similar polarity generated during synthesis. Rapamycin is also known as sirolimus, CAS [53123-88-9]). It is a commercially available macrolide natural product synthesized by *Streptomyces hygroscopicus*. A preferred derivative, 40-O-(2-ethoxyethyl) rapamycin, Umirolimus (INN/USAN), Biolimus A9™ (also known as BA9™) is an active pharmaceutical ingredient developed as a drug coating for coronary stents to prevent smooth muscle cell proliferation and restenosis. Other members of this 'limus' family include everolimus (CAS [159351-69-6]), zotarolimus (CAS [221877-54-9]) and temsirolimus (CAS [162635-04-03]). Members of the family are known to possess immunosuppressive, antifungal, anti-tumor, and/or anti-inflammatory activity in vivo and are useful in the treatment of transplantation rejection, infectious diseases, autoimmune diseases, and conditions characterized by excessive cell proliferation.

The chemical structure of BA9 consists of a 31-membered triene macrolide lactone that preserves the core rapamycin ring structure and differs only in the addition of a side chain at position 40 in which the hydroxyl group of rapamycin has been alkylated with an ethoxyethyl group.

The chemical structure of BA9 compared to sirolimus and other sirolimus derivatives is provided in FIG. 1. BA9 is structurally related to rapamycin (also known as sirolimus). The structure consists of the rapamycin 31-membered macrolide triene lactone ring with ethoxyethylation at position 40.

BA9, like sirolimus, binds to the intracellular immunophilin protein FKBP12. It is believed that the resulting macrolide/FKBP12 complex then binds, in a manner similar to sirolimus, to mTOR, a protein critical for cell cycle progression. Inactivation of mTOR results in suppression of several specific signal transduction pathways and arrest of the cell cycle at the G1 to S phase.

Given the therapeutic value of BA9 and other rapamycin derivatives, improved processes for preparation of this family of active agents is desired. The present invention addresses this and other needs.

BRIEF SUMMARY OF THE INVENTION

The present invention provides method for obtaining a purified, solid compound having a structure according to Formula I:

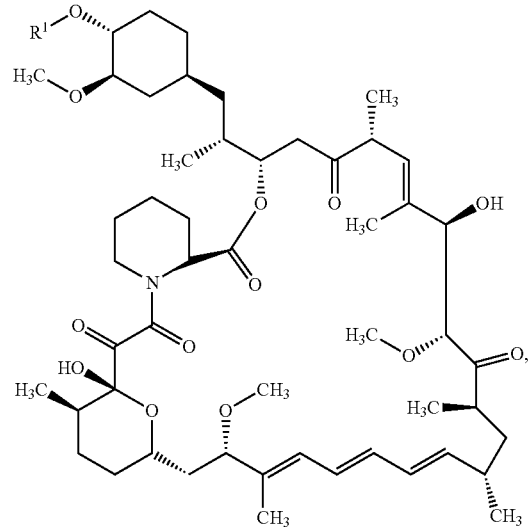

Formula I wherein $R^1$ is selected from the group consisting of H; $R^a$—$(O)_d$—$R^b$, wherein $R^a$ is $C_{1-5}$alkylene, $R^b$ is $C_{1-5}$alkyl or $C_{1-5}$alkylene-OH, and the subscript d is an integer selected from 0-1; $C_{1-5}$alkyl; $C_{6-10}$aryl$C_{1-5}$alkyl; hydroxy$C_{1-5}$alkyl; $C_{6-10}$aryl$C_{1-5}$alkoxy; $C_{1-5}$alkoxy$C_{1-5}$alkyl; acyl; acyl$C_{1-5}$alkyl; amino$C_{1-5}$alkyl; $C_{1-5}$alkylamino$C_{1-5}$alkyl; acylamino$C_{1-5}$alkyl; $C_{1-5}$alkoxycarbonylamino$C_{1-5}$alkyl; and $C_{6-10}$aryl.

The method includes: a) forming a mixture comprising a crude compound having a structure according to Formula I and a non-polar organic solvent under conditions sufficient to dissolve the compound; b) solidifying at least a portion of the compound having the structure according to Formula I; c) separating at least a portion of the solidified compound from the solvent in the mixture; and thereby obtaining the purified, solid compound.

In another embodiment this invention provides for a crystallized form of BA9.

DETAILED DESCRIPTION OF THE INVENTION

I. General

Figure 1:
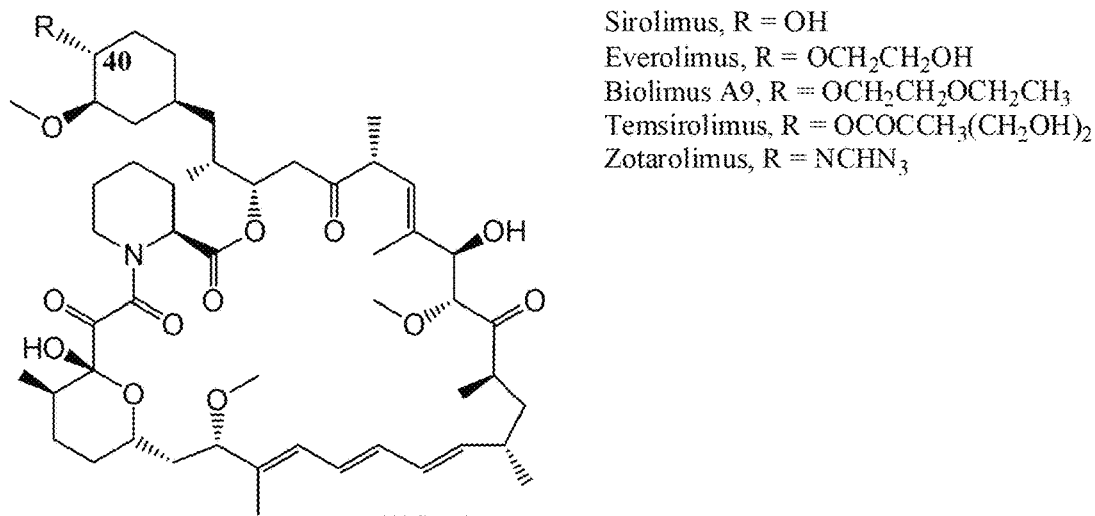
FIG. 1 shows the chemical structures of sirolimus, Biolimus A9, and related derivatives.

The present invention provides improved methods for purifying rapamycin derivatives including Biolimus A9 (BA9). The process includes solidification of a rapamycin derivative from non-polar organic solvents, followed by isolation of the purified product and optional precipitation from a mixture of a polar organic solvent and water. The various steps of the process are described herein. Effective removal of various impurities was discovered to result from the surprisingly simple, economical process. These advantages are described in detail below.

The discovery that a simple solidification by lowering temperature would separate the 40-O derivatives so cleanly from unwanted 40-O derivative impurities and non-40-O derivatives was surprising and unpredictable. It is economically advantageous because the unwanted by-products are often times of a similar polarity to the desired product and they are difficult to separate using large scale chromatography techniques. The methods can be used for preparation of a crystalline form of BA9 that demonstrates superior stability.

II. Definitions

The term "purified" refers to a compound that has been processed to remove impurities. Impurities can include solvents, reagents used to prepare the compound, starting materials, and byproducts of a reaction giving rise to the compound. In some embodiments, a purified compound is substantially free of other species.

The term "crude compound" refers to a mixture containing a desired compound (such as a compound of Formula I as described herein) and at least one other species selected from a solvent, a reagent such as a base, a starting material, and a byproduct of a reaction giving rise to the desired compound.

"Alkyl" refers to a straight or branched, saturated, aliphatic radical having the number of carbon atoms indicated. Alkyl can include any number of carbons, such as $C_{1-2}$, $C_{1-3}$, $C_{1-4}$, $C_{1-5}$, $C_{1-6}$, $C_{1-7}$, $C_{1-8}$, $C_{1-9}$, $C_{1-10}$, $C_{2-3}$, $C_{2-4}$, $C_{2-5}$, $C_{2-6}$, $C_{3-4}$, $C_{3-5}$, $C_{3-6}$, $C_{4-5}$, $C_{4-6}$ and $C_{5-6}$. For example, $C_{1-6}$ alkyl includes, but is not limited to, methyl, ethyl, propyl, isopropyl, butyl, isobutyl, sec-butyl, tert-butyl, pentyl, isopentyl, hexyl, etc. Alkyl can also refer to alkyl groups having up to 20 carbons atoms, such as, but not limited to heptyl, octyl, nonyl, decyl, etc.

"Alkylene" refers to a straight or branched, saturated, aliphatic radical having the number of carbon atoms indicated, and linking at least two other groups, i.e., a divalent hydrocarbon radical. The two moieties linked to the alkylene can be linked to the same atom or different atoms of the alkylene group. For instance, a straight chain alkylene can be the bivalent radical of —$(CH_2)_n$—, where n is 1, 2, 3, 4, 5 or 6. Representative alkylene groups include, but are not limited to, methylene, ethylene, propylene, isopropylene, butylene, isobutylene, sec-butylene, pentylene and hexylene.

"Alkenyl" refers to a straight chain or branched hydrocarbon having at least 2 carbon atoms and at least one double bond. Alkenyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Alkenyl groups can have any suitable number of double bonds, including, but not limited to, 1, 2, 3, 4, 5 or more. Examples of alkenyl groups include, but are not limited to, vinyl (ethenyl), propenyl, isopropenyl, 1-butenyl, 2-butenyl, isobutenyl, butadienyl, 1-pentenyl, 2-pentenyl, isopentenyl, 1,3-pentadienyl, 1,4-pentadienyl, 1-hexenyl, 2-hexenyl, 3-hexenyl, 1,3-hexadienyl, 1,4-hexadienyl, 1,5-hexadienyl, 2,4-hexadienyl, or 1,3,5-hexatrienyl.

"Alkynyl" refers to either a straight chain or branched hydrocarbon having at least 2 carbon atoms and at least one triple bond. Alkynyl can include any number of carbons, such as $C_2$, $C_{2-3}$, $C_{2-4}$, $C_{2-5}$, $C_{2-6}$, $C_{2-7}$, $C_{2-8}$, $C_{2-9}$, $C_{2-10}$, $C_3$, $C_{3-4}$, $C_{3-5}$, $C_{3-6}$, $C_4$, $C_{4-5}$, $C_{4-6}$, $C_5$, $C_{5-6}$, and $C_6$. Examples of alkynyl groups include, but are not limited to, acetylenyl, propynyl, 1-butynyl, 2-butynyl, isobutynyl, sec-butynyl, butadiynyl, 1-pentynyl, 2-pentynyl, isopentynyl, 1,3-pentadiynyl, 1,4-pentadiynyl, 1-hexynyl, 2-hexynyl, 3-hexynyl, 1,3-hexadiynyl, 1,4-hexadiynyl, 1,5-hexadiynyl, 2,4-hexadiynyl, or 1,3,5-hexatriynyl.

"Aryl" refers to an aromatic ring system having any suitable number of ring atoms and any suitable number of rings. Aryl groups can include any suitable number of ring atoms, such as, 6, 7, 8, 9, 10, 11, 12, 13, 14, 15 or 16 ring atoms, as well as from 6 to 10, 6 to 12, or 6 to 14 ring members. Aryl groups can be monocyclic, fused to form bicyclic or tricyclic groups, or linked by a bond to form a biaryl group. Representative aryl groups include phenyl, naphthyl and biphenyl. Other aryl groups include benzyl, having a methylene linking group. Some aryl groups have from 6 to 12 ring members, such as phenyl, naphthyl or biphenyl. Other aryl groups have from 6 to 10 ring members, such as phenyl or naphthyl. Some other aryl groups have 6 ring members, such as phenyl.

"Alkoxy" refers to an alkyl group having an oxygen atom that connects the alkyl group to the point of attachment: alkyl-O—. As for alkyl group, alkoxy groups can have any suitable number of carbon atoms, such as $C_{1-6}$. Alkoxy groups include, for example, methoxy, ethoxy, propoxy, iso-propoxy, butoxy, 2-butoxy, iso-butoxy, sec-butoxy, tert-butoxy, pentoxy, hexoxy, etc.

"Carbonyl" refers to a moiety consisting of a carbon-oxygen double bond (i.e., —C(O)—).

"Acyl" refers to a moiety including a carbonyl group, as described herein, bound to an alkyl group, and alkenyl group, or an alkynyl group, as described herein.

"Forming a mixture" and "contacting" refers to the process of bringing into contact at least two distinct species such that they mix together.

"Non-polar organic solvent" refers to a carbon-based substance that is liquid at or near room temperature, substantially free of water, and characterized by a low dielectric constant (i.e., less than about 5). Examples of non-polar organic solvents that are suitable for use herein include, but are not limited to, hexane, heptane, ligroin, cyclohexane, pentane, n-octane, iso-octane, methylcyclohexane, mineral oil, diethyl ether, diisopropyl ether, methyl t-butyl ether, 1,4-dioxane, chloroform, aromatic hydrocarbon solvents (such as benzene and toluene), cyclopentane, n-octane, iso-octane and methylcyclohexane, for example.

"Alkane organic solvent" refers to a saturated hydrocarbon that is liquid at or near room temperature and substantially free of water. Examples of alkane organic solvents include hexane, heptane, ligroin, cyclohexane, pentane, n-octane, iso-octane, methylcyclohexane, and mineral oil.

"Polar organic solvent" refers to a carbon-based substance that is liquid at or near room temperature, substantially free of water, and characterized by a moderate to high dielectric constant (i.e., greater than about 5). Examples of polar organic solvents include dimethylformamide, dimethyl sulfoxide, propylene carbonate, acetonitrile, methanol, ethanol, isopropanol, t-butanol, tetrahydrofuran, and acetone.

"Solubilizing" refers to the process of dissolving a solid form of a substance in a solvent to form a solution. The entirety of a solid substance, or any fraction thereof, can be caused to dissolve. Undissolved material can be present in the solvent in the form of a suspension "Cooling" refers to the process of reducing the temperature of a substance or mixture of substances.

"Solidifying" refers to the process of causing a compound in a solution to coalesce into a solid form of the substance. The entirety of a compound in a solution, or any fraction thereof, can be caused to solidify. The solid form can be an amorphous or crystalline substance. "Precipitating" refers to solidifying a substance in an amorphous form.

"Solid" refers to a condensed form of a compound that is not a gas, liquid, or solution. A solid can include one species or a mixture of two or more species. A solid compound can be a crystalline form, an amorphous form, a glass, a foam, or a mixture of two or more forms.

"Crystalline form" refers to a solid form of a compound wherein the constituent molecules are packed in a regularly ordered, repeating pattern. A crystalline form can be triclinic, monoclinic, orthorhombic, tetragonal, trigonal, hexagonal, or cubic. A crystalline form can contain one or more regions, i.e., grains, with distinct crystal boundaries. A crystalline solid can contain two or more crystal geometries.

"Amorphous form" refers to a solid form of a compound having no definite crystal structure, i.e., lacking a regularly ordered, repeating pattern of constituent molecules.

"Unsolidified" refers to a compound that is not in a solid form. An unsolidified compound can be, for example, dissolved in a solution or suspended in a colloid.

"Separating" refers to the process of isolating at least a portion of a compound from a mixture containing the compound and at least one other substance. The isolated compound is substantially free at least one of the other substances present in the mixture.

"Reflux" refers to the process of boiling of a solvent while condensing the solvent vapors and returned the condensed solvent to the boiling pot. Reflux is generally conducted at or near the boiling point of a solvent or mixture of solvents at a particular pressure.

"Drying" refers to the removal of a liquid species, such as a solvent, from a compound. Drying is generally conducted by heating the compound, reducing the pressure under which the compound is stored, or both.

The terms "about" and "around," as used herein to modify a numerical value, indicate a close range surrounding that explicit value. If "X" were the value, "about X" or "around X" would indicate a value from 0.9X to 1.1X, and more preferably, a value from 0.95X to 1.05X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.98X."

III. Embodiments of the Invention

The present invention provides method for obtaining a purified, solid compound having a structure according to Formula I:

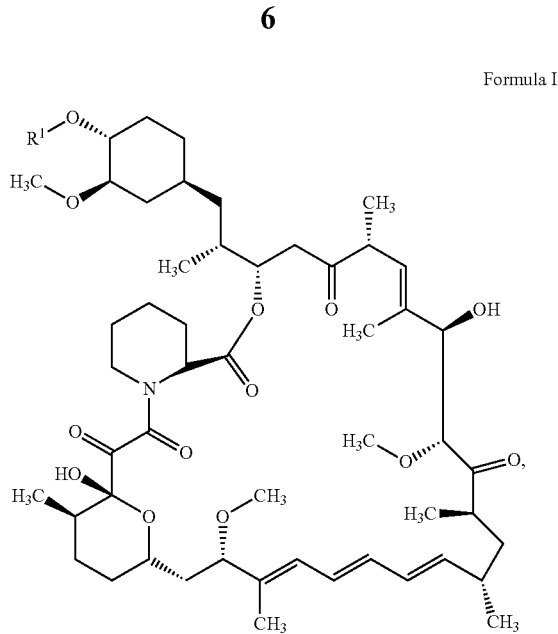

Formula I wherein $R^1$ is selected from the group consisting of H; $R^a$—$(O)_d$—$R^b$, wherein $R^a$ is $C_{1-5}$alkylene, $R^b$ is $C_{1-5}$alkyl or $C_{1-5}$alkylene-OH, and the subscript d is an integer selected from 0-1; $C_{1-5}$alkyl; $C_{6-10}$aryl$C_{1-5}$alkyl; hydroxy$C_{1-5}$alkyl; $C_{6-10}$aryl$C_{1-5}$alkoxy; $C_{1-5}$alkoxy$C_{1-5}$alkyl; acyl; acyl$C_{1-5}$alkyl; amino$C_{1-5}$alkyl; $C_{1-5}$alkylamino$C_{1-5}$alkyl; acylamino$C_{1-5}$alkyl; $C_{1-5}$alkoxycarbonylamino$C_{1-5}$alkyl; and $C_{6-10}$aryl.

The method includes: a) forming a mixture comprising a crude compound having a structure according to Formula I and a non-polar organic solvent under conditions sufficient to dissolve the compound; b) solidifying at least a portion of the compound having the structure according to Formula I; c) separating at least a portion of the solidified compound from the solvent in the mixture; and thereby obtaining the purified, solid compound.

Figure 2:
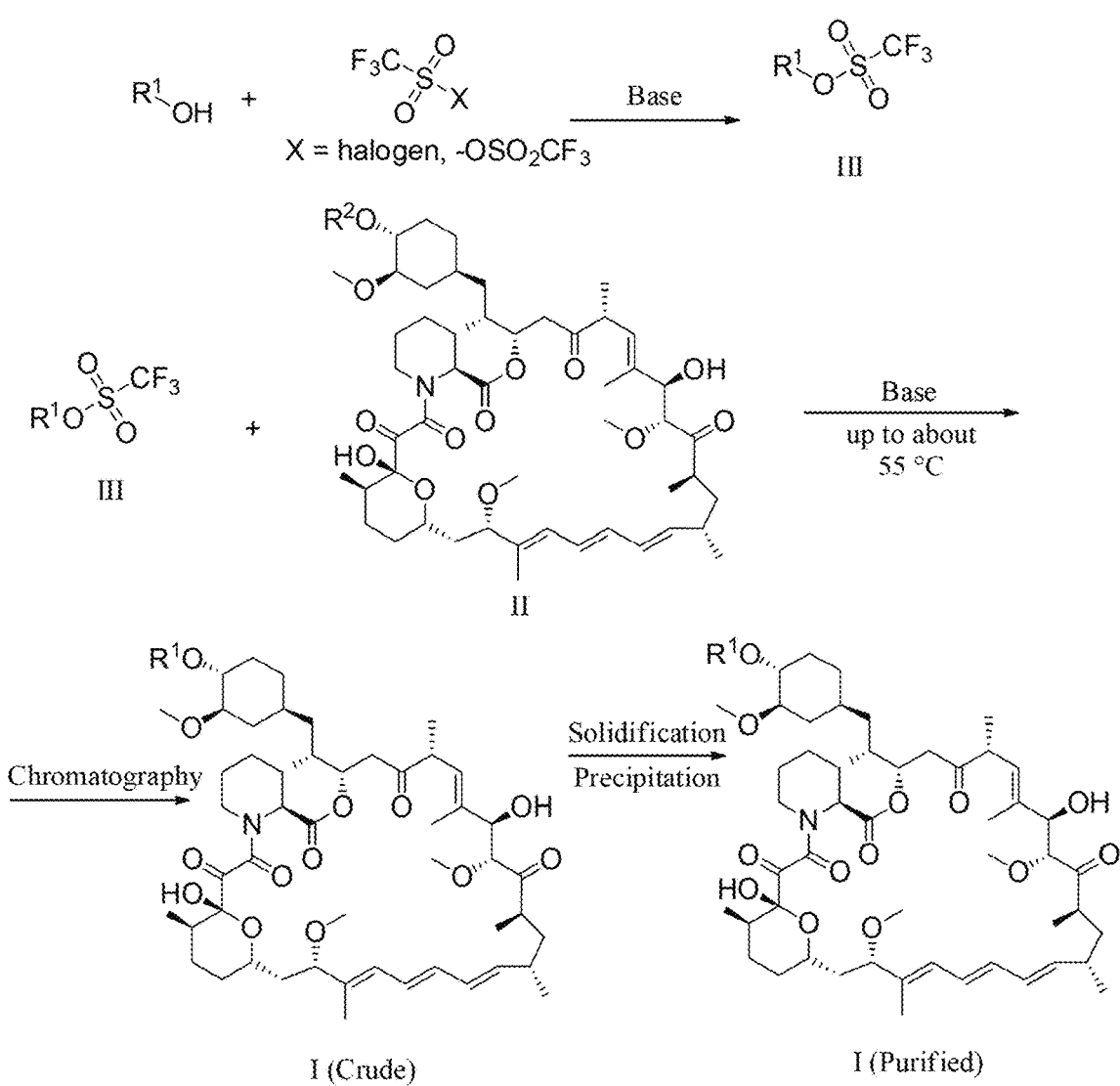
FIG. 2 shows a scheme for the preparation of rapamycin derivatives and purification of the derivatives according to the methods of the invention.

In some embodiments, the crude compounds used in the methods of the invention are prepared according to the process shown in FIG. 2. The process includes reaction of rapamycin with a suitable triflate at a controlled temperature, followed by work-up and optional isolation of the products. Isotopically labeled starting materials, such as deuterated materials, can be used to prepare isotopically labeled rapamycin derivatives. The methods of the invention generally include separating a compound of Formula I from a reaction mixture including solvents, reagents including bases, and starting materials according to Formula II and Formula III (see FIG. 2). Suitable separation techniques include, but are not limited to, filtration of a solidified compound of Formula I, centrifugation of a solidified compound of Formula I, distillation, liquid extraction, sublimation, and chromatographic techniques. Examples of chromatographic techniques include, but are not limited to, normal-phase column chromatography (i.e., silica gel column chromatography), reverse-phase column chromatography, and thin-layer chromatography. Two or more separation techniques can be conducted in combination to separate the compound of Formula I. In some embodiments, the chromatography is silica gel chromatography with hexane or heptane and ethyl acetate.

Chromatography and other separation techniques provide crude compounds of Formula I with varying levels of purity. The crude compounds contain a compound of Formula I, as well as at least one other species selected from a solvent, a reagent such as a base, a starting material according to Formula II or Formula III, and byproduct(s) of the rapamycin derivatization reaction. In general, a crude compound contains at least 40% of a compound of Formula I by weight. In certain embodiments, a crude compound contains at least 50% of a compound of Formula I by weight. The crude compound can include, for example, from about 40% to about 99%, or from about 50% to about 99%, or from about 75% to about 95%, of a compound of Formula I by weight. In some embodiments, the crude compound contains from about 90% to about 95% of a compound of Formula I by weight.

Any suitable solvent can be used in the methods of the invention. In general, suitable solvents are non-polar. Preferred solvents include alkane organic solvents (i.e., saturated hydrocarbon solvents) and alkene organic solvents. Examples of alkane organic solvents include, but are not limited to, hexane, heptane, ligroin (i.e. petroleum ether), cyclohexane, octane, pentane, and mineral oil (including paraffinic oils and naphthenic oils). In some embodiments, the non-polar organic solvent is selected from hexane, heptane, ligroin, cyclohexane, pentane, n-octane, iso-octane, methylcyclohexane, mineral oil, diethyl ether, diisopropyl ether, methyl t-butyl ether, 1,4-dioxane, chloroform, benzene, toluene, cyclopentane, n-octane, iso-octane and methylcyclohexane, and mixtures thereof. In some embodiments, the non-polar organic solvent is selected from hexane, heptane, ligroin, octane, cyclohexane and mixtures thereof. In some embodiments, the non-polar organic solvent is hexane. In some embodiments, the non-polar organic solvent is heptane. Other non-polar solvents can be useful in the methods of the invention depending on the properties of the particular rapamycin derivative.

Any suitable quantity of solvent can be used in the methods of the invention. In general, the amount of solvent used is sufficient to dissolve the compound of Formula I. Typically, the amount of solvent ranges from about 1 part to about 500 parts, by weight, per part crude compound. The solvent:crude ratio can be from about 1:1 to about 500:1, or from about 50:1 to about 250:1 by weight. The solvent:crude ratio can be about 95:1, or about 100:1, or about 105:1, or about 110:1, or about 115:1, or about 120:1 by weight. In some embodiments, the solvent:crude ratio is about 110:1 by weight. The crude weight in the solvent:crude ratio can refer to the total weight of the crude mixture or to the weight of the compound of Formula I in the mixture as determined, for example, by HPLC or another analytical technique.

The mixture containing the crude compound of Formula I and the non-polar organic solvent is formed under conditions sufficient to dissolve the crude compound. The mixture can be heated, if necessary, to dissolve the compound. Any suitable temperature can be used to dissolve the compound of Formula I. One of skill in the art will appreciate that the heating temperature will depend, in part, on one or more factors including the polarity of the solvent, the quantity of the solvent, the level of purity of the crude compound, and the specific structure of the compound of Formula I. Such factors will also determine, to an extent, the length of time required to dissolve the crude compound. Any suitable length of the time can be used, ranging from a few minutes to several hours. For example, the mixture containing the crude compound and the organic solvent can be mixed, with or without heating, for about 10 minutes, or about 20 minutes, or 30 minutes, or about 40 minutes, or about 1 hour. Accordingly, some embodiments of the invention provide a method for obtaining a purified, solid compound of Formula I as described above, wherein forming the mixture containing the crude compound and the organic solvent includes heating the mixture. In some embodiments, forming the mixture includes heating the mixture to a temperature of from about 35° C. to about 100° C. In some embodiments, forming the mixture includes heating the mixture to reflux.

In order to separate the purified compound of Formula I from the other components in the crude material, the compound of Formula I is solidified and isolated from the mother liquor of the organic solvent mixture. Solidifying the compound of Formula I can include cooling the mixture. The mixture can be cooled to any suitable temperature. One of skill in the art will appreciate that the cooling temperature can depend, in part, on the solubility of the compound of Formula I in the organic solvent, as well as the quantity of the solvent used in the process. In some embodiments, cooling the mixture includes cooling the mixture to a temperature of from about −78° C. to about 25° C. In some embodiments, cooling the mixture includes cooling the mixture to a temperature of about 15° C. The cooling can be conducted over any suitable length of time, typically ranging from a few minutes to several hours. For example, the mixture can be slowly cooled to a desired temperature over a period of three to four hours. After the mixture reaches a desired temperature, it can be held at or around that temperature for an additional period ranging from a few minutes to several hours.

Separating the solidified compound from the organic solvent can be accomplished by a number of techniques, including passing the mixture through a filter to isolate the solid material from the mother liquor or centrifuging the mixture and removing the mother liquor supernatant. The separated solid material can be triturated with additional portions of the organic solvent to remove residual impurities, if present. The mother liquor can include varying quantities of the compound of Formula I that was not solidified, however. If the mother liquor contains such unsolidified material, the unsolidified material can be recovered, e.g., by removal of the organic solvent under vacuum, and resubjected to the dissolution/solidification steps. Accordingly, some embodiments of the invention provide methods as described above, further including isolating any unsolidified crude compound having a structure according to Formula I. In some embodiments, the method further includes conducting steps a), b), and c), as described above, with the unsolidified crude compound.

The purified, solid compound can be obtained in a number of forms using the methods of the invention. The compound of Formula I can be obtained, for example, as a powder, a glass, or a foam. The compound of Formula I can be obtained as a crystalline form or an amorphous form. The compound can be obtained as a mixture of two or more forms. In some embodiments, the purified solid compound is obtained in a crystalline form. A crystalline form is characterized by constituent molecules that are packed in a regularly ordered, repeating pattern and generally extending in all three spatial dimensions. In some embodiments, the purified solid compound is obtained in an amorphous form. An amorphous form is a solid form having no definite crystal structure, i.e., lacking a regularly ordered, repeating pattern of constituent molecules.

One of skill in the art will appreciate that the solid form of the purified compound will depend to an extent on the structure of the compound and the characteristics of the solvent used in the dissolution/solidification steps. The purified, solid compound—obtained in a particular form as described above—can be further processed to obtain a more preferred solid form if necessary. In some embodiments, the method as described above further includes: d) solubilizing the solidified compound in a polar organic solvent to form a solution; e) contacting the solution with water to precipitate at least a portion of the compound; and f) drying the precipitated compound.

Any suitable polar organic solvent can be used to dissolve the purified, solid compound. In general, the most suitable polar organic solvents are miscible with water. Examples of polar organic solvents include, but are not limited to, dimethylformamide, dimethyl sulfoxide, propylene carbonate, acetonitrile, methanol, ethanol, isopropanol, t-butanol, tetrahydrofuran, acetone, and mixtures thereof. Preferred polar organic solvents have boiling points below 100° C. In some embodiments, the polar organic solvent is selected from methanol, ethanol, isopropanol, t-butanol, tetrahydrofuran, and acetone. In some embodiments, the polar organic solvent is methanol. In general, the ratio of polar organic solvent to the purified, solid compound ranges from about 1:1 by weight to about 500:1 by weight. The ratio of polar organic solvent to the purified, solid compound can be, for example, about 2:1 by weight or about 3:1 by weight.

Water is added to the solution of the purified compound of Formula I in the polar organic solvent, generally in an amount sufficient to precipitate the compound of Formula I from the solution. Any suitable amount of water can be used in the methods of the invention. Typically, the ratio of water to polar organic solvent ranges from about 1:20 to about 20:1 by volume. The ratio of water to polar organic solvent can be, for example, about 10:1. Following precipitation, the precipitated compound can be isolated via filtration or centrifugation as described above. Alternatively, the mixture can be frozen and the solvent/water mixture can be removed from the precipitate via sublimation. In some embodiments, the precipitated compound is dried under reduced pressure. Any suitable pressure and drying time can be used to remove traces of water and solvent from the precipitated compounds. Drying can be conducted, for example, under reduced pressure until the weight of the precipitated compound remains constant.

The methods of the present invention can be used to purify a number of macrolide derivatives. Macrolides, including those having structures according to Formula II in FIG. 2, are polyketide natural products and synthetic analogs characterized by a macrocyclic lactone ring. The methods of the invention are particularly useful for preparation of rapamycin derivatives Biolimus A9 (BA9), everolimus, zotarolimus, and temsirolimus. Some embodiments of the invention provide methods for obtaining a purified solid compound of Formula I as described above, wherein $R^1$ is selected from H and $R^a$—$(O)_d$—$R^b$. In some embodiments, $R^1$ is selected from H, $CH_2$—$CH_2$—OH, and $CH_2$—$CH_2$—O—$CH_2$—$CH_3$. In some embodiments, $R^1$ is $CH_2$—$CH_2$—O—$CH_2$—$CH_3$. Other macrolide derivatives can also be purified using the methods of the invention.

The methods of the invention provide highly pure compounds of Formula I. In general, the purified, solid compounds are at least 90% pure. In some embodiments, the purified, solid compounds are at least 95% pure. In some embodiments, the purity of the purified, solid compound is increased by from about 1% to about 20% with respect to the crude compound. The methods of the invention can provide greater increases in the purity of the purified, solid compound depending, in part, on factors such as the structure of the particular rapamycin derivative and the starting purity of the crude material. In some embodiments, the purity of the purified, solid compound is increased by from about 1% to about 10% with respect to the crude compound. In some embodiments, the purity of the purified, solid compound is increased by about 3% with respect to the crude compound.

In some embodiments, the methods of the invention also include contacting the purified, solid compound with an anti-solvent composition. The methods of the invention can include combining a solution of the purified compound with an anti-solvent composition. In general, the anti-solvent composition contains a non-polar organic solvent in which the compound is insoluble or sparingly soluble at or below room temperature. The anti-solvent composition can contain, for example, diethyl ether, diisopropyl ether, methyl t-butyl ether, ligroin, cyclohexane, octane, hexane, heptane, and mixtures thereof. In some embodiments, the anti-solvent composition includes diethyl ether, diisopropyl ether, hexane, heptane, or any combination thereof. In some embodiments, the anti-solvent composition includes hexane, heptane, ligroin, octane, cyclohexane, and mixtures thereof. In some embodiments, the methods include contacting the purified compound with an anti-solvent composition and obtaining a crystalline solid form of the compound.

In a related aspect, the invention provides a crystalline form of 40-O-(2-ethoxyethyl) rapamycin. The crystalline form exhibits superior stability as compared to the amorphous form.

Figure 6:
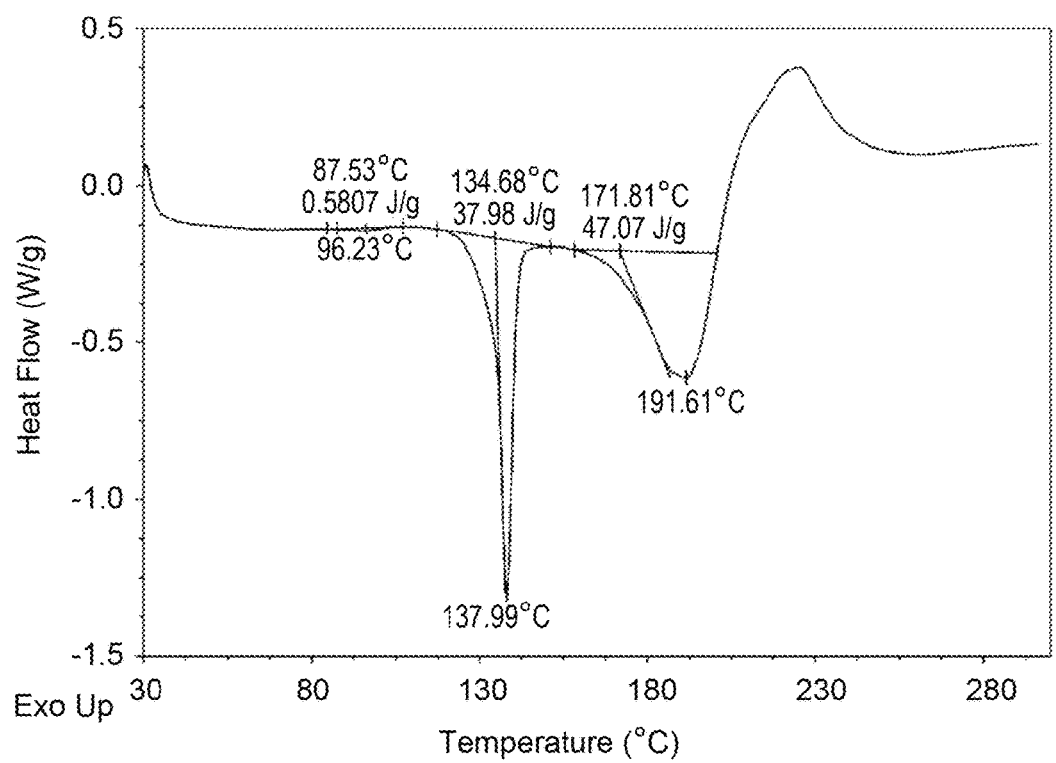
FIG. 6 shows a DSC thermogram observed for BA9 Lot 2B.

In some embodiments, the crystalline form of 40-O-(2-ethoxyethyl) rapamycin is such that the differential scanning calorimetry thermogram thereof shows one or more local minima at around 138° C. and around 192° C. In some embodiments, the thermogram shows local minima at or around 137.9° C. and 191.6° C. In some embodiments, the thermogram is substantially in accordance with FIG. 6 as shown herein.

In some embodiments, the crystalline form of 40-O-(2-ethoxyethyl) rapamycin is such that the infrared spectrum thereof shows one or more peaks at or around the wavenumbers selected from 2967.1 $cm^{-1}$, 2931.7 $cm^{-1}$, 2863.3 $cm^{-1}$, 1745.9 $cm^{-1}$, 1718.8 $cm^{-1}$, 1645.7 $cm^{-1}$, 1619.0 $cm^{-1}$, 1451.2 $cm^{-1}$, 1378.2 $cm^{-1}$, 1189.4 $cm^{-1}$, 1073.9 $cm^{-1}$, and 988.1 $cm^{-1}$. In some embodiments, the infrared spectrum shows five or more peaks at or around the wavenumbers selected from 2967.1 $cm^{-1}$, 2931.7 $cm^{-1}$, 2863.3 $cm^{-1}$, 1745.9 $cm^{-1}$, 1718.8 $cm^{-1}$, 1645.7 $cm^{-1}$, 1619.0 $cm^{-1}$, 1451.2 $cm^{-1}$, 1378.2 $cm^{-1}$, 1189.4 $cm^{-1}$, 1073.9 $cm^{-1}$, and 988.1 $cm^{-1}$. In some embodiments, the infrared spectrum shows ten or more peaks at or around the wavenumbers selected from 2967.1 $cm^{-1}$, 2931.7 $cm^{-1}$, 2863.3 $cm^{-1}$, 1745.9 $cm^{-1}$, 1718.8 $cm^{-1}$, 1645.7 $cm^{-1}$, 1619.0 $cm^{-1}$, 1451.2 $cm^{-1}$, 1378.2 $cm^{-1}$, 1189.4 $cm^{-1}$, 1073.9 $cm^{-1}$, and 988.1 $cm^{-1}$. In some embodiments, the infrared spectrum is substantially in accordance with FIG. 12 as shown herein.

Figure 5:
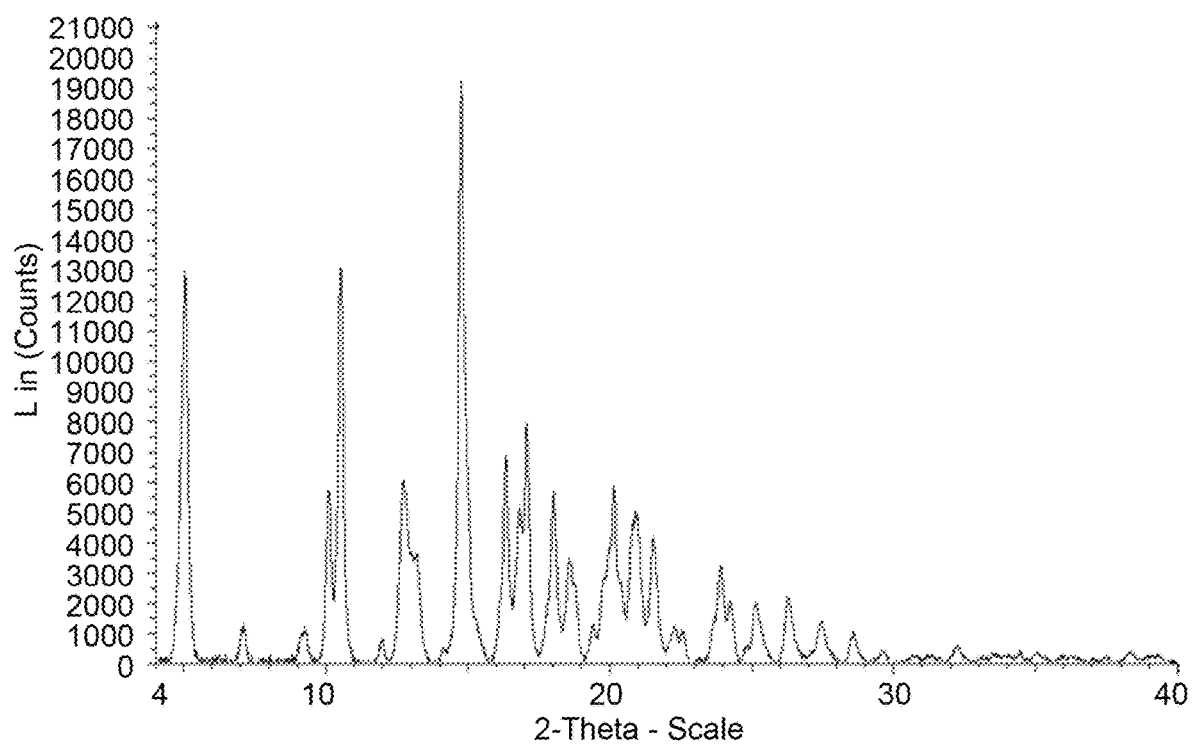
FIG. 5 shows an XRPD pattern observed for BA9 Lot 2B.

In some embodiments, the crystalline form of 40-O-(2-ethoxyethyl) rapamycin is such that the X-ray powder diffraction pattern thereof shows one or more diffraction peaks at or around the angles (2θ) selected from the group consisting of 5.00°, 7.06°, 9.22°, 10.07°, 10.50°, 11.94°, 12.71°, 13.15°, 14.73°, 16.33°, 16.80°, 17.07°, 18.01°, 18.57°, 19.42°, 19.81°, 20.16°, 20.44°, 20.93°, 21.55°, 22.29°, 22.58°, 23.92°, 24.26°, 24.83°, 25.17°, 26.32°, 27.48°, 28.60°, and 32.28°. In some of these embodiments, the X-ray powder diffraction pattern thereof shows 10 or more diffraction peaks at or around the angles (2θ) selected from the group consisting of 5.00°, 7.06°, 9.22°, 10.07°, 10.50°, 11.94°, 12.71°, 13.15°, 14.73°, 16.33°, 16.80°, 17.07°, 18.01°, 18.57°, 19.42°, 19.81°, 20.16°, 20.44°, 20.93°, 21.55°, 22.29°, 22.58°, 23.92°, 24.26°, 24.83°, 25.17°, 26.32°, 27.48°, 28.60°, and 32.28°. In still some of these embodiments, the X-ray powder diffraction pattern thereof shows 25 or more diffraction peaks at or around the angles (2θ) selected from the group consisting of 5.00°, 7.06°, 9.22°, 10.07°, 10.50°, 11.94°, 12.71°, 13.15°, 14.73°, 16.33°, 16.80°, 17.07°, 18.01°, 18.57°, 19.42°, 19.81°, 20.16°, 20.44°, 20.93°, 21.55°, 22.29°, 22.58°, 23.92°, 24.26°, 24.83°, 25.17°, 26.32°, 27.48°, 28.60°, and 32.28°. In some embodiments, the X-ray powder diffraction pattern shows one or more diffraction peaks at or around the angles (2θ) shown in Table 4. In some embodiments, the X-ray powder diffraction pattern shows 10 or more, or 25 or more, diffraction peaks at or around the angles (2θ) shown in Table 4. In some embodiments, the X-ray powder diffraction pattern is substantially in accordance with FIG. 5 as shown herein.

IV. Examples

Example 1. Purification of BA9

Following synthesis of BA9 according to FIG. 2, a chromatography gradient containing n-hexane and ethyl acetate in various ratios was used as a first purification step. Ninety fractions were collected during chromatography. Fractions 15-30 were combined to form Lot A (containing 3.6 g of BA9). Fractions 31-50 were combined to form Lot B (containing 4.6 g of BA9). Fractions 51-70 were combined to form Lot C (containing 3.4 g of BA9). Fractions 1-14 and 71-90 were combined to form Lot E (containing 2.2 g of BA9). The various lots contained 92.0-94.9% BA9, as determined by HPLC and summarized in Table 1 below. Relative amounts are expressed as AUC % (area under the curve), i.e., the fraction of the total signal that corresponds to a single peak (corresponding, in turn, to a single species, or two or more species with similar/identical absorbance wavelengths and retention times) in a given chromatogram. Impurities 1-9 shown in Table 1 are numbered according to increasing retention time; retention times were reproducible across experiments.

TABLE 1

Lots of purified BA9 from the second column chromatography

| | Relative Quantity (% AUC, as determined by HPLC) of BA9 and Impurities 1-9 | | | | | | | | | |
|---|---|---|---|---|---|---|---|---|---|---|
| Lot | 1 | 2 | 3 | BA9 | 4 | 5 | 6 | 7 | 8 | 9 |
| A | <0.1 | 0.09 | 0.58 | 91.5 | 0.15 | 0.80 | 0.82 | 3.74 | 0.47 | 1.40 |
| B | <0.1 | 0.08 | 0.89 | 92.8 | 0.27 | 0.79 | 0.63 | 3.11 | 0.37 | 0.69 |
| C | 0.34 | 0.10 | 1.16 | 88.7 | 1.20 | 1.36 | 0.84 | 4.91 | 0.82 | 0.43 |
| D | <0.1 | <0.1 | <0.1 | 85.1 | 1.16 | 1.67 | 1.17 | 6.32 | 1.16 | 3.37 |
| E | <0.39 | 0.14 | 0.83 | 76.0 | 3.46 | 2.31 | 2.12 | 8.07 | 1.51 | 3.93 |

To Lot B, a viscous crude material containing 4.6 g of BA9, was added n-hexane (490 g) at room temperature. While the mixture was vigorously stirred, it was heated to reflux (~70° C.) within 30 minutes. The viscous material turned to an easily-stirred, suspended powder at ~56° C. and then to a clear solution after 5 minutes stirring at reflux. The system was refluxed for 20 minutes and then allowed to cool to room temperature within 3 hours. The cooling caused precipitation of a white solid. The suspension was additionally stirred at 25-15° C. for 2 hours. The suspension was then filtered, and the isolated solid was washed on the filter with 50 g of n-hexane. The solid was then dried in vacuo to a constant weight (yield=3.4 g, 74% recovery of BA9).

The results of purification are summarized in Table 2. The precipitation procedure lowered the amounts of the late-eluting BA9 impurities (i.e., impurities 5-9). The amount of impurity 4, as well as of other more polar impurities, were similar for the starting lot and the purified/precipitated lot of BA9.

TABLE 2

HPLC analysis of BA9 Lot B (refer to Table 1) purified by precipitation from hot n-hexane

| | Relative Quantity (% AUC, as determined by HPLC) of BA9 and Impurities 1-9 | | | | | | | | | |
|---|---|---|---|---|---|---|---|---|---|---|
| Portion | 1 | 2 | 3 | BA9 | 4 | 5 | 6 | 7 | 8 | 9 |
| Starting Lot (Lot B) | <0.1 | 0.08 | 0.89 | 92.8 | 0.27 | 0.79 | 0.63 | 3.11 | 0.37 | 0.69 |
| Purified, solid BA9 (Lot B) | 0.12 | 0.09 | 0.87 | 96.0 | 0.32 | 0.32 | 0.32 | 1.79 | <0.1 | 0.19 |
| Mother liquor after purification | <0.1 | 0.21 | 0.63 | 68.4 | <0.1 | 4.36 | 4.11 | 12.00 | 2.75 | 3.39 |

Lots A, C and E were also precipitated from refluxing n-hexane. For this, a similar weight ratio of 1:110 between the weight of BA9 (established by quantitative HPLC analysis) and n-hexane was used. The amounts and purities of the four lots of BA9 obtained by the n-hexane purification are summarized in Table 3. As it is evident from Table 3, the purification of portions of BA9 by precipitation from refluxing n-hexane generated two new lots A and B (presented in Table 3) containing BA9 with improved levels of purity (i.e., >95%). The lots were obtained using the surprisingly simple, economical method of the invention. Table 3 shows improved values related to Table 1.

TABLE 3

HPLC Analysis of portions of purified BA9 by precipitation from refluxing n-hexane - refer to corresponding portions from Table 1.

| Lot | Relative Quantity (% AUC, as determined by HPLC) of BA9 and Impurities 1-9 | | | | | | | | | | Weight |
|---|---|---|---|---|---|---|---|---|---|---|---|
| | 1 | 2 | 3 | BA9 | 4 | 5 | 6 | 7 | 8 | 9 | |
| A[1] | <0.1 | 0.07 | 0.59 | 96.5 | 0.16 | 0.25 | 0.27 | 1.46 | 0.06 | 0.41 | 2.9 g |
| B[1] | 0.12 | 0.09 | 0.87 | 96.0 | 0.32 | 0.32 | 0.32 | 1.79 | <0.1 | 0.19 | 3.4 g |
| C[1] | 0.56 | <0.1 | 1.06 | 94.0 | 1.06 | 0.30 | 1.03 | 1.92 | <0.1 | <0.1 | 1.6 g |
| E[1] | 0.68 | 0.17 | 1.12 | 92.6 | 2.26 | 0.21 | 0.49 | 2.02 | <0.1 | 0.27 | 1.2 g |

[1]Product of n-hexane precipitation.

The discovery that a simple solidification by lowering temperature would separate the 40-O derivatives so cleanly from unwanted impurities/byproducts was surprising and unpredictable. It is economically advantageous because the unwanted by-products are often of a similar polarity to the desired product and require labor-intensive, high-cost large scale chromatography techniques for removal.

Example 2. Preparation and Characterization of BA9 Solid Forms

Batch profiling and polymorph screening methods. BA9 Lots 2A and 2B were purified using precipitation from n-hexanes as described above. After the purification process, Lot 2A (82.9 g) was dissolved in methanol (190 g) and precipitated by adding the methanol solution to water. The combined methanolic solution was transferred to an addition funnel and then slowly charged within 1 hour and 15 minutes into vigorously stirred water for injection (2.18 kg) in a reactor at a temperature range of 0-5° C. After completion of the addition of the methanolic solution of BA9, the resulting white suspension was stirred for an additional 15 minutes at the same temperature range. The precipitated BA9 was isolated in 84.8% yield (purity was 96.3% as determined by HPLC). The suspension was then filtered, and the isolated white solid was washed on the filter. Lot 2A was characterized by XRPD and DSC and Lot 2B was characterized by XRPD, DSC, optical microscopy, and infrared (IR) spectroscopy. Lot 2A was found to be amorphous, as assessed by XRPD. Lot 2B was found to be crystalline, as assessed by XRPD, and the crystalline form was designated as Form I. A dynamic vapor sorption (DVS) experiment was run on Lot 2B.

Two stock solutions of BA9 Lot 2A in EtOAc and acetone were prepared. These solutions were dispensed into glass vials and placed in a vacuum oven for evaporation to dryness. The solids obtained after drying were dissolved in different solvents/solvent mixtures and stirred overnight. Any solids obtained after the dissolution-recrystallization process were analyzed as wet cake by XRPD.

Anti-solvent crystallization experiments were carried out by dissolving Lot 2A in 6 different organic solvents. Hexane was added as the anti-solvent. If no solids were observed, the solutions were allowed to stir at room temperature.

Results and Discussion

Batch Profiling.

Figure 3:
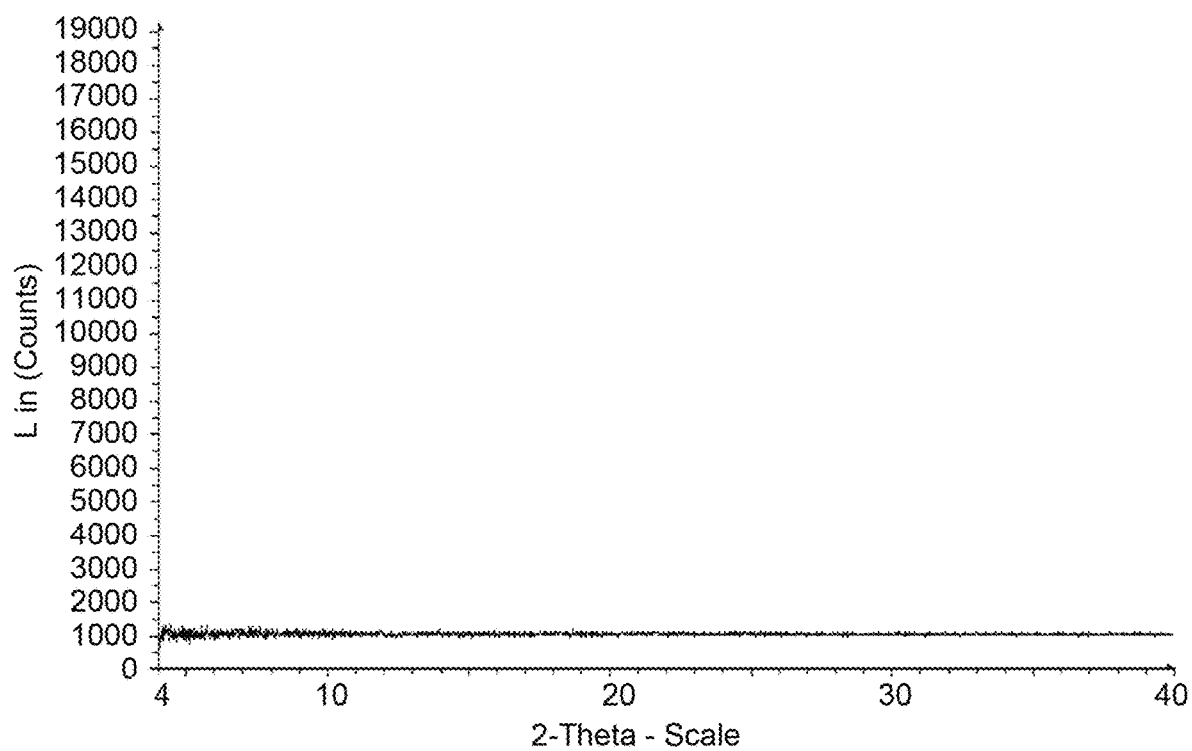
FIG. 3 shows an X-ray powder diffraction (XRPD) pattern observed for BA9 Lot 2A.
Figure 4:
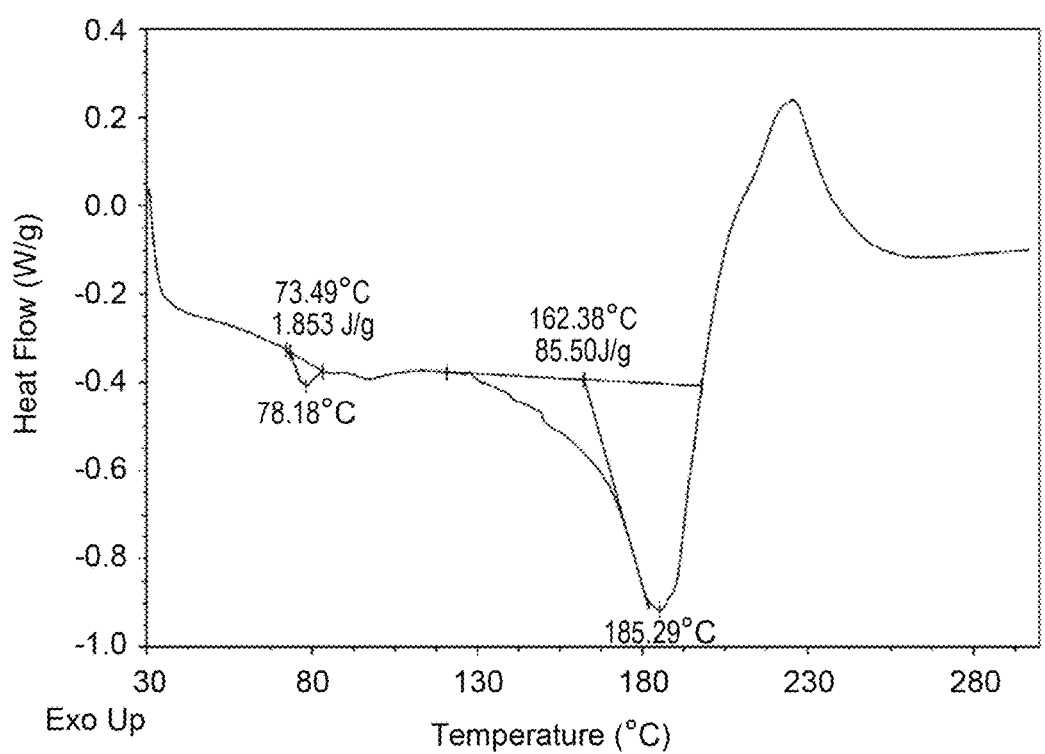
FIG. 4 shows a differential scanning calorimetry (DSC) thermogram observed for BA9 Lot 2A.
Figure 7:
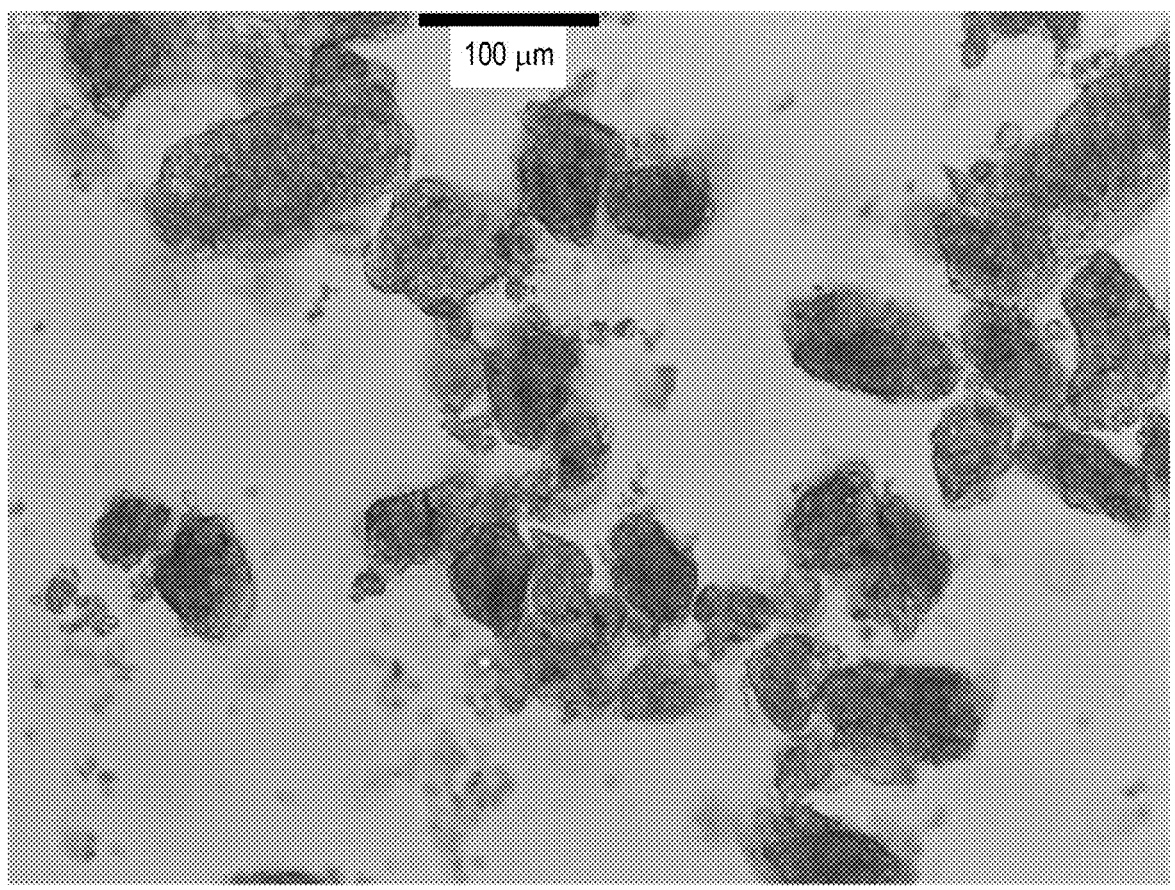
FIG. 7 shows an optical micrograph observed for BA9 Lot 2B.
Figure 12:
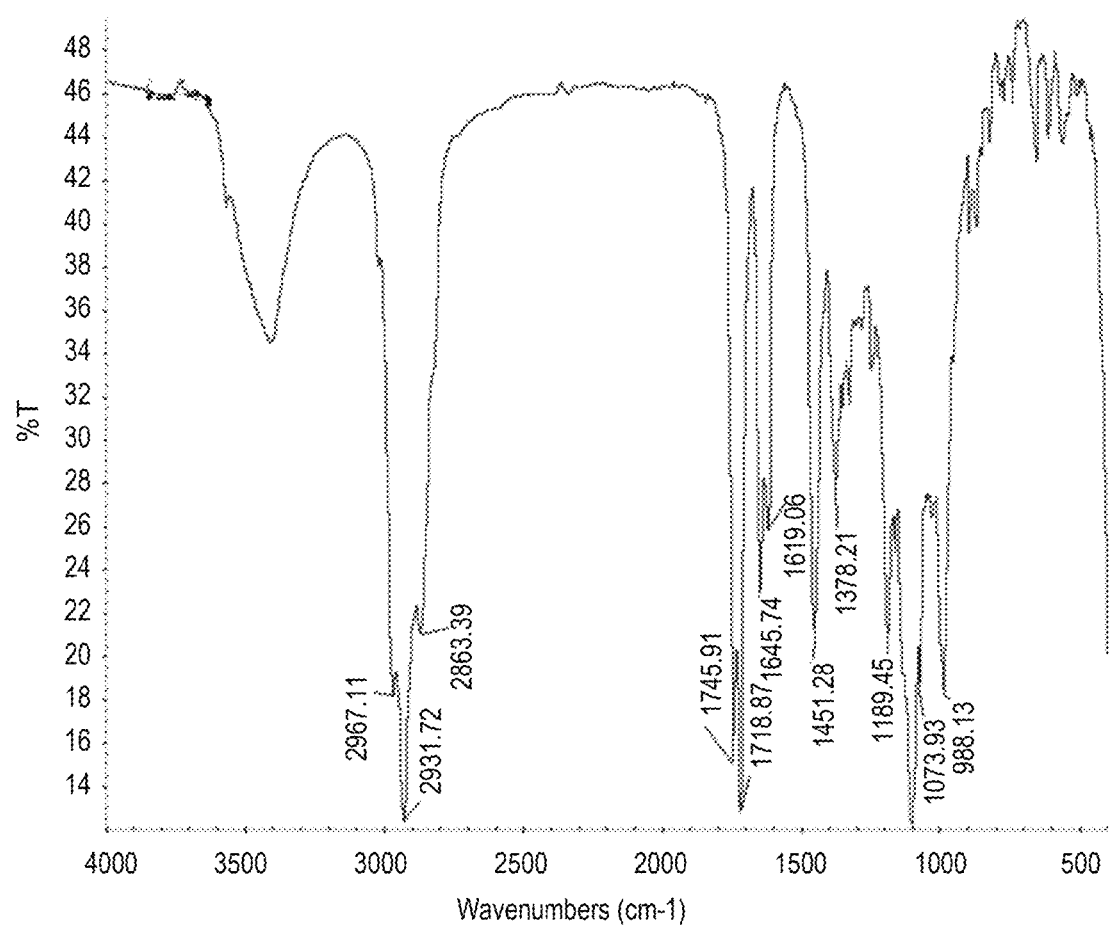
FIG. 12 shows an infrared spectrum of BA9 Form I, obtained using a sample in a KBr pellet.

BA9 Lot 2A was characterized by XRPD (FIG. 3) and DSC (FIG. 4) and Lot 2B was characterized by XRPD (FIG. 5), DSC (FIG. 6), optical microscopy (FIG. 7), and infrared spectroscopy (FIG. 12). Lot 2A is amorphous by XRPD. Lot 2B is crystalline by XRPD and was designated as Form I. Diffraction angles (2θ) for Form I are listed in Table 4.

TABLE 4

BA9 Form I XRPD Data

| Angle, 2θ | d spacing | Intensity, % |
|---|---|---|
| 5.00 | 17.66 | 67.7 |
| 7.06 | 12.51 | 6.6 |
| 9.22 | 9.58 | 5.7 |
| 10.07 | 8.77 | 28.8 |
| 10.50 | 8.42 | 67.6 |
| 11.94 | 7.40 | 3.8 |
| 12.71 | 6.96 | 31.2 |
| 13.15 | 6.73 | 18.3 |
| 14.73 | 6.01 | 100 |
| 16.33 | 5.42 | 34.5 |
| 16.80 | 5.27 | 25.1 |
| 17.07 | 5.19 | 39.8 |
| 18.01 | 4.92 | 27.5 |
| 18.57 | 4.77 | 16.3 |
| 19.42 | 4.57 | 4.3 |
| 19.81 | 4.48 | 11.6 |
| 20.16 | 4.4 | 26.4 |
| 20.44 | 4.34 | 8.9 |
| 20.93 | 4.24 | 21.4 |
| 21.55 | 4.12 | 18.5 |
| 22.29 | 3.99 | 4.9 |
| 22.58 | 3.93 | 4.6 |
| 23.92 | 3.72 | 15.9 |
| 24.26 | 3.67 | 10.1 |
| 24.83 | 3.58 | 2.4 |
| 25.17 | 3.54 | 9.4 |
| 26.32 | 3.38 | 10.8 |
| 27.48 | 3.24 | 6 |
| 28.60 | 3.12 | 4.7 |
| 32.28 | 2.77 | 2.4 |

Figure 8:
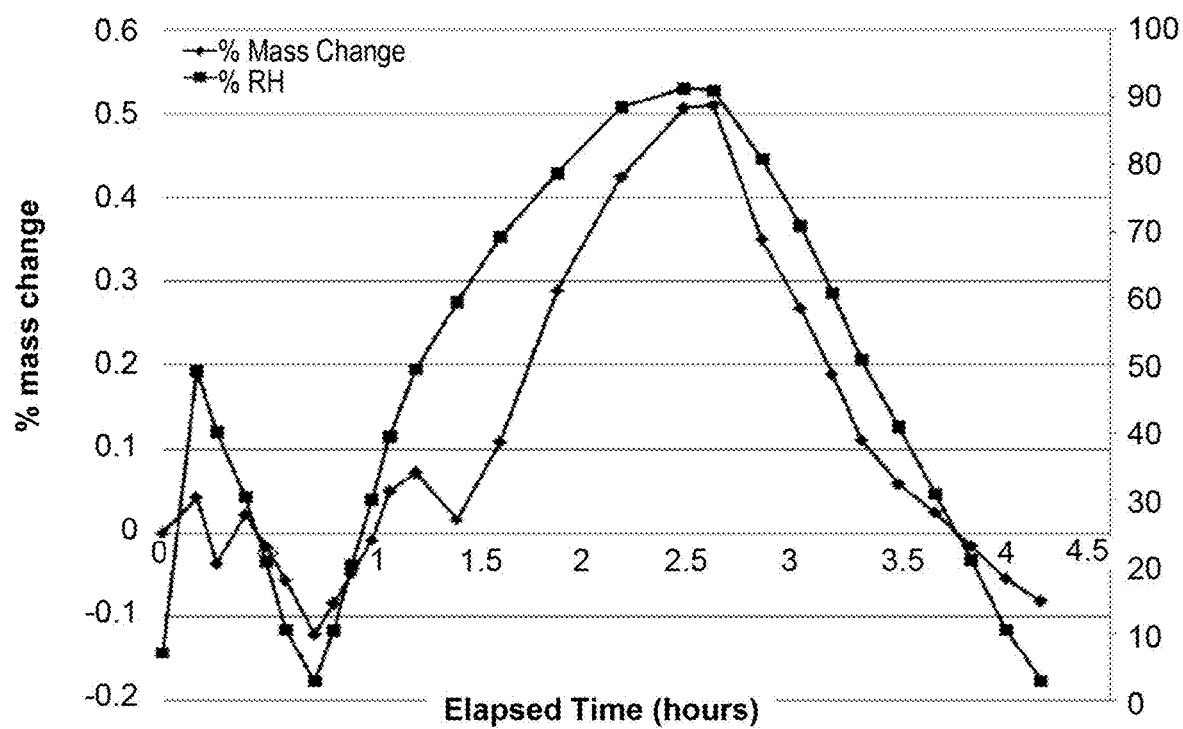
FIG. 8 shows a dynamic vapor sorption (DVS) kinetic plot observed for BA9 Lot 2B.
Figure 9:
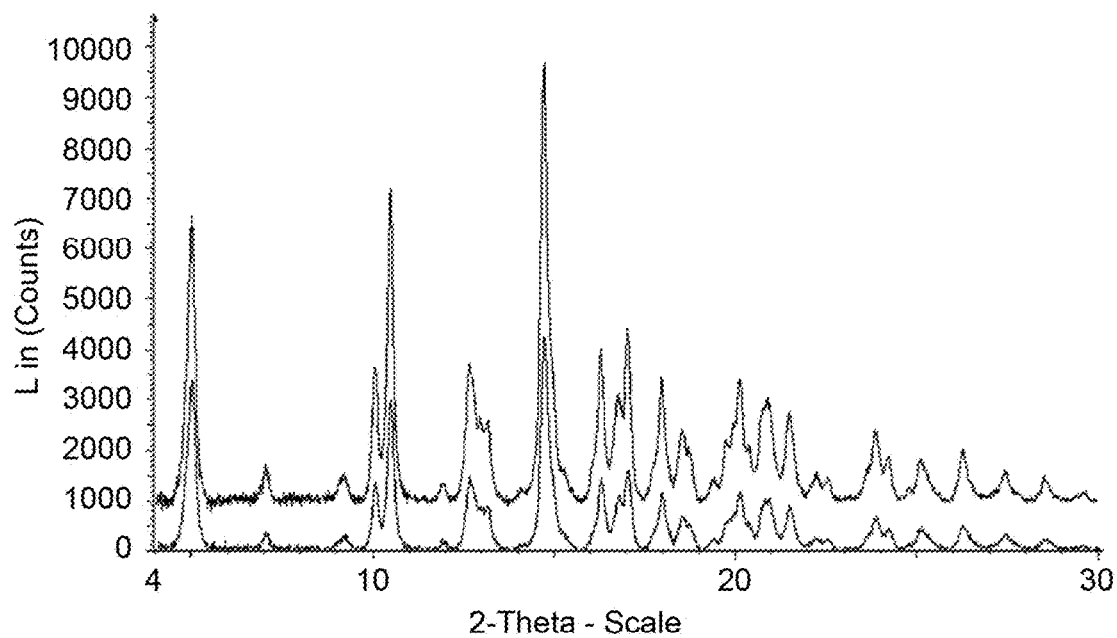
FIG. 9 shows a XRPD pattern overlay observed for BA9 Lot 2B after a DVS experiment and a reference pattern of BA9 Form I.

A DVS experiment was run on Lot 2B. The increase in mass of the sample was ~0.5% at 90% RH. The kinetic plot is shown in FIG. 8. The post DVS sample was analyzed by XRPD and confirmed as Form I. FIG. 9 shows an overlay of the XRPD patterns of the post-DVS sample and a reference pattern of Form I.

Polymorph screening. Two stock solutions of BA9 Lot 2A (100 mg/ml) in ethyl acetate (Stock A in Table 4) and acetone (Stock B in Table 4) were prepared by dissolving ~380 mg of the material in 3.8 ml of the respective solvents. These solutions were dispensed into 22 glass vials (0.4 ml in each vial, 11 vials per stock solution) and placed in a vacuum oven at room temperature for evaporation to dryness. After 2 days of drying ~40 mg material were obtained in each vial as a cracked gel.

Figure 10:
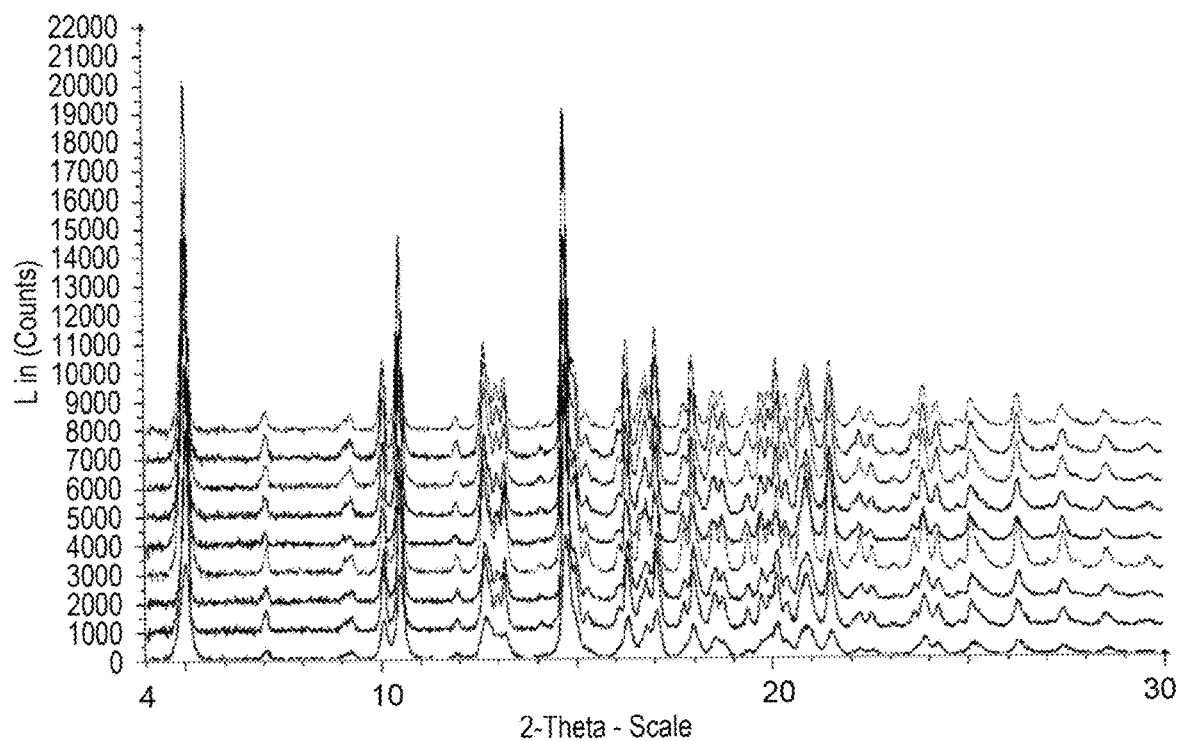
FIG. 10 shows and overlay of the XRPD patterns obtained from solvent slurries and a reference pattern of BA9 Form I.

Eleven different solvents/solvent mixtures were added to the vials (160 μl each) and the solutions obtained were allowed to stir at room temperature. After overnight stirring, if solids had precipitated out, then the slurry was filtered and the solids obtained were analyzed as wet cake by XRPD. The results of these experiments are shown in Table 5. FIG. 10 shows an overlay of the XRPD patterns obtained in the recrystallization experiments and a reference pattern of Form I.

TABLE 5

Summary of Dissolution/Recrystallization Experiments

| Sample No. | Solvent | Stock A | Stock B |
|---|---|---|---|
| 3 | DEE | Form I | Form I |
| 4 | DIPE | Form I | Form I |
| 5 | MTBE | Clear Solution | Clear Solution |
| 6 | Hexane | Form I | Form I |
| 7 | Heptane | Form I | Form I |
| 8 | MEK | Clear Solution | Clear Solution |
| 9 | Toluene | Clear Solution | Clear Solution |
| 10 | IPA:Water 1:1 | N/A (gel precipitate) | N/A (gel precipitate) |
| 11 | Acetone:Water 1:1 | N/A (gel precipitate) | N/A (gel precipitate) |

Figure 11:
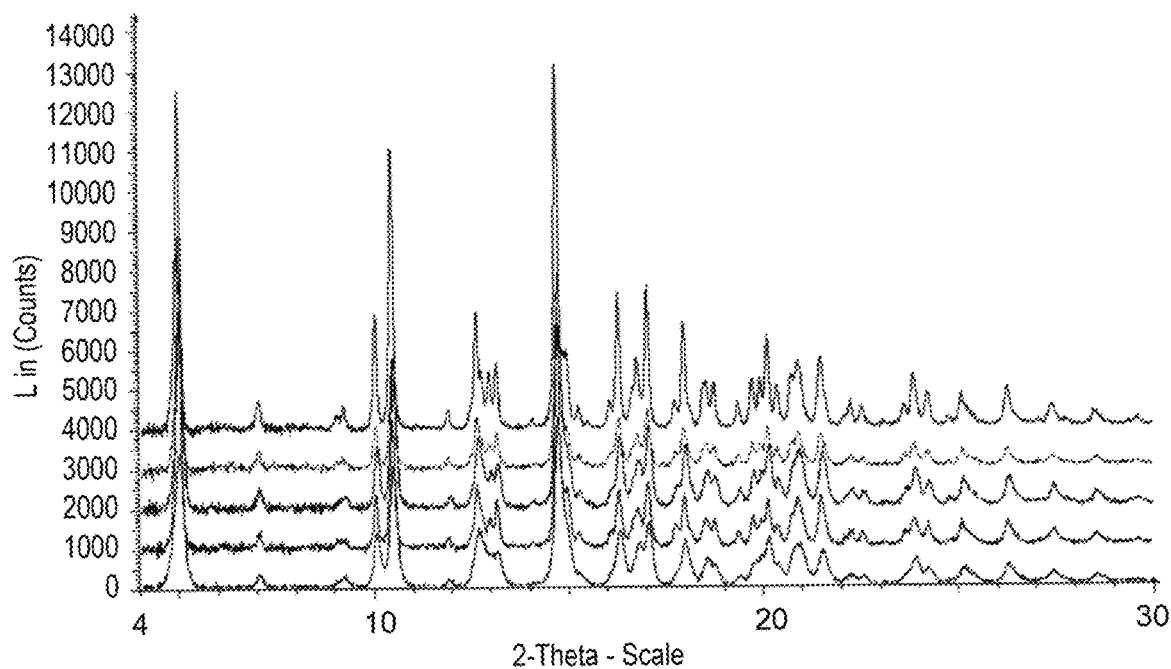
FIG. 11 shows an overlay of the XRPD patterns obtained in anti-solvent crystallization experiments and a reference pattern of BA9 Form I.

Anti-solvent crystallization experiments were carried out by dissolving ~40 mg each of Lot 2A in 6 different organic solvents (200 μl each). Hexane was added as the antisolvent in steps of 200 μl until solids precipitated out or 1.6 ml of hexane had been added. If no solids were observed the solutions were allowed to stir at room temperature. The results of these experiments are shown in Table 6. FIG. 11 shows an overlay of the XRPD patterns obtained in the anti-solvent crystallization experiments and a reference pattern of Form I.

TABLE 6

Summary of Anti-Solvent Crystallization Experiments.

| Sample No. | Solvent | Vol. of Hexane Added | Form as determined by XRPD | Comment |
|---|---|---|---|---|
| 12 | Ethyl Acetate | 1.6 mL | Form I | Precipitated after a few min. of stirring |
| 13 | Acetone | 1.6 mL | N/A | No solids |
| 14 | IPA | 1.6 mL | Form I | Precipitated after 30-45 min. of stirring |
| 15 | EtOH | 1.6 mL | N/A | No solids |
| 16 | THF | 1.6 mL | Form I | Precipitated after >1 hr. of stirring |
| 17 | DEE | 400 μL | Form I | Gel-like precipitate changed to white solid after few min. of stirring |

Example 3. Crystalline BA9 Exhibits Superior Stability

Photolysis studies were performed on amorphous and crystalline BA9 (i.e, Form I). After exposure to a minimum of 1.2 million lux hours and not less than 200 W-hours/m² per ICH Q1B, both the crystalline and amorphous BA9 exhibited significant increases in degradation compounds with similar retention times. However, photolysis of crystalline BA9 resulted in less overall major degradants as determined by HPLC, refer to Table 7. Furthermore, purity assay measurements showed that after photolysis, the crystalline BA9 assayed at 70.2% pure, which was substantially higher than the 16.3% assay purity of the amorphous BA9.

The improvement in stability of the crystalline BA9 as compared to the amorphous BA9 is further supported by the comparison of the Dark Controls, which were maintained at standard laboratory temperature and same conditions as the test samples with the exception of exposure to light for the duration of the study. The crystalline Dark Control (assay 98.0%) also exhibited improved stability when compared with the amorphous Dark Control (88.2%). Therefore, the crystalline BA9 was shown to be significantly more stable than amorphous BA9 under photolysis and storage under laboratory conditions.

TABLE 7

Summary of Photostability Experiments

| | Crystalline BA9 | | | Amorphous BA9 | | |
|---|---|---|---|---|---|---|
| | T = 0 Control | Photolysis VIS/UV | Dark Control | T = 0 Control | Photolysis VIS/UV | Dark Control |
| Purity Assay, % | 97.7 | 70.2 | 98.0 | 98.0 | 16.3 | 88.2 |

| RT (min) | Major Degradants, % | | | Major Degradants, % | | |
|---|---|---|---|---|---|---|
| 4.2 | | 0.76 | 0.01 | | 1.30 | — |
| 4.5 | | 2.00 | 0.08 | | 7.40 | 0.72 |
| 4.9 | | 2.60 | 0.41 | | 1.20 | 0.31 |
| 6.2 | | 0.94 | 0.09 | | 2.50 | 0.20 |
| 7.9 | | 0.07 | — | | 2.20 | — |
| 10.4 | | 0.15 | 0.03 | | 1.70 | 0.44 |
| 10.7 | | 0.69 | 0.06 | | 0.94 | 1.40 |
| 11.0 | | 0.51 | 0.67 | | 2.60 | 0.39 |

Oxidation studies were performed on amorphous and crystalline BA9. After exposure to 30% $H_2O_2$ for 3 hours, both the crystalline and amorphous BA9 exhibited increases in degradation compounds with similar HPLC retention times. However, oxidative degradation of crystalline BA9 resulted in lower levels of major degradants overall. In addition, assay measurements showed that after oxidative degradation, the crystalline BA9 exhibited a weight loss of 3.4% (relative to a control sample), which was substantially lower than the weight loss of 6.5% exhibited by amorphous BA9. It is therefore apparent that amorphous BA9 is more susceptible to oxidative degradation.

The superior photostability and chemical stability of crystalline BA9 can prevent loss of valuable material during storage and fabrication of coated medical devices. The advantages of the new crystalline form, as well as the economy and surprising simplicity of the methods for preparation of the crystalline form, help to maintain the integrity of the drug-coated products while decreasing the cost and complexity of their production.

Although the foregoing has been described in some detail by way of illustration and example for purposes of clarity and understanding, one of skill in the art will appreciate that certain changes and modifications can be practiced within the scope of the appended claims. In addition, each reference provided herein is incorporated by reference in its entirety to the same extent as if each reference was individually incorporated by reference.

What is claimed is:

1. A method for obtaining a crystalline 40-O-(2-ethoxyethyl) rapamycin, the method comprising:
   a) forming a mixture consisting essentially of crude 40-O-(2-ethoxyethyl) rapamycin and a non-polar organic solvent under conditions sufficient to dissolve the 40-O-(2-ethoxyethyl) rapamycin,
   wherein the crude 40-O-(2-ethoxyethyl) rapamycin contains at least about 90% of 40-O-(2-ethoxyethyl) rapamycin by weight,
   wherein the dielectric constant of the non-polar organic solvent is less than about 5,
   and wherein forming the mixture comprises heating the mixture;
   b) solidifying at least a portion of the 40-O-(2-ethoxyethyl) rapamycin in a crystalline form, wherein the solidifying comprises cooling the mixture; and
   c) separating at least a portion of the solidified 40-O-(2-ethoxyethyl) rapamycin from the solvent in the mixture,
   wherein the solidified 40-O-(2-ethoxyethyl) rapamycin it at least about 95% pure;
   thereby obtaining the crystalline 40-O-(2-ethoxyethyl) rapamycin.

2. The method of claim 1, wherein the non-polar organic solvent is selected from the group consisting of hexane, heptane, methyl t-butyl ether, ligroin, octane, cyclohexane, and mixtures thereof.

3. The method of claim 2, wherein the non-polar organic solvent is hexane.

4. The method of claim 2, wherein the non-polar organic solvent is heptane.

5. The method of claim 1, wherein the mixture in step a) is heated to a temperature of from about 35° C. to about 100° C.

6. The method of claim 1, wherein the mixture in step a) is heated to reflux.

7. The method of claim 1, wherein cooling the mixture in step b) comprises cooling the mixture to a temperature of from about −78° C. to about 25° C.

8. The method of claim 1, wherein the X-ray powder diffraction pattern of the crystalline 40-O-(2-ethoxyethyl) rapamycin shows one or more diffraction peaks at or around the angles (2θ) selected from the group consisting of 5.00°, 7.06°, 9.22°, 10.07°, 10.50°, 11.94°, 12.71°, 13.15°, 14.73°, 16.33°, 16.80°, 17.07°, 18.01°, 18.57°, 19.42°, 19.81°, 20.16°, 20.44°, 20.93°, 21.55°, 22.29°, 22.58°, 23.92°, 24.26°, 24.83°, 25.17°, 26.32°, 27.48°, 28.60°, and 32.28°.

9. The method of claim 8, wherein the X-ray powder diffraction pattern shows 10 or more diffraction peaks at or around the angles (2θ) selected from the group consisting of 5.00°, 7.06°, 9.22°, 10.07°, 10.50°, 11.94°, 12.71°, 13.15°, 14.73°, 16.33°, 16.80°, 17.07°, 18.01°, 18.57°, 19.42°, 19.81°, 20.16°, 20.44°, 20.93°, 21.55°, 22.29°, 22.58°, 23.92°, 24.26°, 24.83°, 25.17°, 26.32°, 27.48°, 28.60°, and 32.28°.

10. The method of claim 8, wherein the X-ray powder diffraction pattern shows 25 or more diffraction peaks at or around the angles (2θ) selected from the group consisting of 5.00°, 7.06°, 9.22°, 10.07°, 10.50°, 11.94°, 12.71°, 13.15°, 14.73°, 16.33°, 16.80°, 17.07°, 18.01°, 18.57°, 19.42°, 19.81°, 20.16°, 20.44°, 20.93°, 21.55°, 22.29°, 22.58°, 23.92°, 24.26°, 24.83°, 25.17°, 26.32°, 27.48°, 28.60°, and 32.28°.

11. The method of claim 9, wherein the X-ray powder diffraction pattern is substantially in accordance with FIG. 5.

12. The method of claim 1, wherein the differential scanning calorimetry thermogram of the crystalline 40-O-(2-ethoxyethyl) rapamycin shows one or more local minima at around 138° C. and around 192° C.

13. The method of claim 12, wherein the thermogram shows local minima at 137.9° C. and 191.6° C.

14. The method of claim 12, wherein the thermogram is substantially in accordance with FIG. 6.

15. The method of claim 1, wherein the infrared spectrum of the crystalline 40-O-(2-ethoxyethyl) rapamycin shows one or more peaks at or around the wavenumbers selected from the group consisting of 2967.1 $cm^{-1}$, 2931.7 $cm^{-1}$, 2863.3 $cm^{-1}$, 1745.9 $cm^{-1}$, 1718.8 $cm^{-1}$, 1645.7 $cm^{-1}$, 1619.0 $cm^{-1}$, 1451.2 $cm^{-1}$, 1378.2 $cm^{-1}$, 1189.4 $cm^{-1}$, 1073.9 $cm^{-1}$, and 988.1 $cm^{-1}$.

16. The method of claim 15, wherein the infrared spectrum shows five or more peaks at or around the wavenumbers selected from the group consisting of 2967.1 $cm^{-1}$, 2931.7 $cm^{-1}$, 2863.3 $cm^{-1}$, 1745.9 $cm^{-1}$, 1718.8 $cm^{-1}$, 1645.7 $cm^{-1}$, 1619.0 $cm^{-1}$, 1451.2 $cm^{-1}$, 1378.2 $cm^{-1}$, 1189.4 $cm^{-1}$, 1073.9 $cm^{-1}$, and 988.1 $cm^{-1}$.

17. The method of claim 15, wherein the infrared spectrum shows ten or more peaks at or around the wavenumbers selected from 2967.1 $cm^{-1}$, 2931.7 $cm^{-1}$, 2863.3 $cm^{-1}$, 1745.9 $cm^{-1}$, 1718.8 $cm^{-1}$, 1645.7 $cm^{-1}$, 1619.0 $cm^{-1}$, 1451.2 $cm^{-1}$, 1378.2 $cm^{-1}$, 1189.4 $cm^{-1}$, 1073.9 $cm^{-1}$, and 988.1 $cm^{-1}$.

18. The method of claim 15, wherein the infrared spectrum is substantially in accordance with FIG. 12.

\* \* \* \* \*